United States Patent [19]
Trerice et al.

[11] Patent Number: 5,109,201
[45] Date of Patent: Apr. 28, 1992

[54] METHOD AND ASSOCIATED APPARATUS FOR DETERMINING CARBON CONTENT IN FLY ASH

[76] Inventors: Douglas N. Trerice, 661 Surfside Dr., Pittsburgh, Pa. 15239; Charles R. Buffler, R.R. 1, Box 15A, Marlborough, N.H. 03455

[21] Appl. No.: 448,125

[22] Filed: Dec. 8, 1989

[51] Int. Cl.$^5$ .................................... G01N 22/00
[52] U.S. Cl. .................... 324/642; 324/639; 73/28.01
[58] Field of Search .............. 324/637, 639, 641, 642; 73/61 R, 28.01, 28.04, 61.1 R; 110/216, 165 R, 165 A; 340/627

[56] References Cited

U.S. PATENT DOCUMENTS

| | | | |
|---|---|---|---|
| 4,484,133 | 11/1984 | Riggin | 324/637 |
| 4,580,441 | 4/1986 | Sakurai et al. | 324/639 X |
| 4,641,083 | 2/1987 | Ohno et al. | 324/637 |
| 4,663,507 | 5/1987 | Trerice | 219/10.55 M |
| 4,705,409 | 11/1987 | Trerice | 219/10.55 M X |

FOREIGN PATENT DOCUMENTS 872094 7/1961 United Kingdom .

OTHER PUBLICATIONS

Paper by Trerice & DiGioia entitled "A New Method for Improving the Saleability of Fly Ash" presented in New Orleans, La. Mar. 15-17, 1988.

Primary Examiner—Jack B. Harvey
Attorney, Agent, or Firm—Arnold B. Silverman; David V. Radack

[57] ABSTRACT

A method and apparatus for determining carbon content in fly ash providing a source of fly ash and a microwave interrogation chamber. A quantity of fly ash is introduced into the interrogation chamber and exposed to microwave energy. The amount of carbon in the fly ash is determined by measuring the amount of microwave energy exposed to the fly ash, the amount of energy transmitted through the fly ash, and the amount reflected therefrom in order to determine the amount of energy absorbed. The concentration of fly ash is preferably determined by determining the weight of the fly ash and determining the percentage of carbon content in the fly ash. The method is particularly useful in respect of monitoring carbon content in fly ash of boiler exhaust gases. The system may also be employed to determine the fly ash glass content of fly ash.

32 Claims, 4 Drawing Sheets

METHOD AND ASSOCIATED APPARATUS FOR DETERMINING CARBON CONTENT IN FLY ASH

BACKGROUND OF THE INVENTION

1. Field of the Invention

The present invention provides a system for determination of the carbon concentration in fly ash and, more specifically, it permits automated determination of the amount of carbon in fly ash by interrogating the fly ash with microwave energy and determining the amount of microwave energy absorbed thereby.

2. Description of the Prior Art

The importance of determining the carbon content of fly ash, such as is produced in coal burning boilers, has long been known. For example, fly ash can be a marketable combustion product for utility companies which burn coal in order to generate electrical energy. In general, when carbon levels are greater than about 3 percent in fly ash, the fly ash becomes unsalable. Fly ash is known to be usable in the cement replacement market.

When the carbon content is too high to permit marketing of the fly ash to such users as the cement replacement market or the ready mixed concrete producers, not only is there a loss of potential sales revenue, but also there is the burden of disposal costs.

The quantity of fly ash carbon may also be viewed as a loss of potential fuel due to less than complete burning. Determination of unburned carbon by conventional methods is time consuming, and as a result, is not available to plant operators on a timely basis. If there were a way of determining carbon content promptly, adjustments could be made to the combustion process that would minimize carbon content in the fly ash, i.e., unburned fuel loss.

Among other known uses of fly ash are as fillers in plastics and asphalt, as a source of activated carbon for water and sludge treatment, as a source of magnetite for coal cleaning as well as for use in structural fills and backfill embankments, landfill covers, soil amendment and pavement base courses.

It has been known that the carbon content in fly ash can be determined by employing microwave energy which passes through a fly ash sample and measuring the unabsorbed microwave energy. In one embodiment, temperature differential in a waterwall is measured. An electronic device, sensitive to microwave power is also suggested in a general manner. See U.S. Pat. Nos. 4,663,507 and 4,705,409. See also, a paper entitled "A New Method For Improving the Salability of Fly Ash" by Trerice and DiGioia presented at the American Public Power Association Engineering and Operations Workshop in New Orleans, La. on Mar. 15-17, 1988 which shows collection and interrogation apparatus.

Despite the foregoing known systems, there remains a real and substantial need for improved means for measuring the carbon content of fly ash in an efficient and timely manner.

SUMMARY OF THE INVENTION

The method of the present invention involves providing a source of fly ash and subjecting a quantity of the fly ash to an interrogation chamber wherein it is exposed to microwave radiation. A quantity of fly ash is introduced into the interrogation chamber and exposed to the microwave energy for a predetermined period of time. The amount of carbon in the fly ash is determined by measuring the amount of microwave energy exposed to the fly ash, the amount of microwave energy passing through the fly ash and the amount of microwave energy reflected by the fly ash. These determinations may be employed to ascertain the amount of microwave radiation absorbed by the fly ash. These data permit a determination of the percentage of carbon in fly ash to be made.

Computers may be employed to compute the amount of microwave energy absorbed by the fly ash along with the amount transmitted and reflected and the percentage concentration of carbon can be determined. The quantity of fly ash delivered to the interrogation chamber may be measured.

The apparatus of the present system preferably has a collection system which will capture a gaseous stream having entrained fly ash, a means for separating the fly ash from the gaseous stream, and returning the gaseous stream to a main duct. The main duct may advantageously be the exhaust duct from a coal fired boiler. A quantity of fly ash is interrogated within the interrogation chamber by means of the microwave energy. Means are provided for determining (a) the amount of microwave energy being delivered to the interrogation chamber, (b) the amount of microwave energy passing through the fly ash, and (c) the amount of microwave energy reflected by the fly ash and converting this information into a determination of the quantity of carbon and the quantity of fly ash.

It is an object of the present invention to provide a method and associated apparatus for measuring the carbon content in fly ash in an efficient and rapid, automated manner.

It is a further object of the present invention to provide such a system wherein precise determination of the carbon content may be obtained through the use of microwave energy.

It is a further object of the present invention to provide such a system that determines the amount of the fly ash sample being analyzed.

It is another object of the present invention to provide a process wherein carbon content of fly ash may be determined through a sampling procedure which extracts fly ash laden exhaust gases at a velocity corresponding to the velocity of the same through the main exhaust duct.

It is a further object of the present invention to provide such a system which resists undesired escape of microwave radiation from the apparatus.

These and other objects of the invention will be more fully understood from the following description of the invention with reference to the illustrations appended hereto.

DESCRIPTION OF THE PREFERRED EMBODIMENTS

The term "fly ash" as used herein refers to solid products of combustion, including, but not limited to coal combustion.

Referring once again to FIG. 1, there is shown a block diagram of an overview of the system of the present invention. There is shown a main duct 2 through which the boiler exhaust gases pass in the direction indicated by the arrow F. The exhaust gases pass through the main duct interior toward an electrostatic precipitator or other particulate collection device (not shown).

Figure 1:
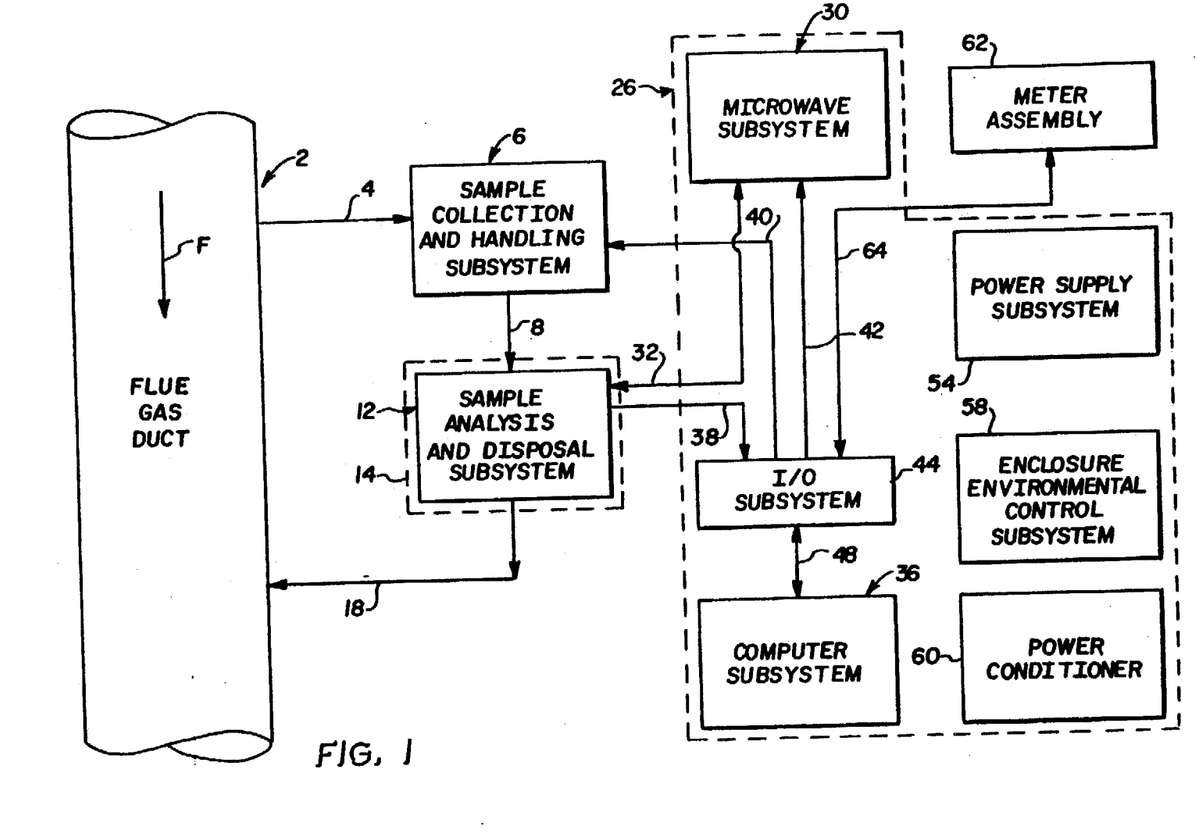
FIG. 1 is a system architecture diagram showing the system for employing microwave energy to determine the carbon concentration of fly ash.

The flue gas to be analyzed will be withdrawn from the main duct by any suitable means known to those skilled in the art. The gas which is removed contains particles of fly ash entrained therein and will pass through duct 4 to sample collection and handling subsystem 6. This subsystem 6 is responsible for collecting fly ash samples and releasing the sample to the interrogation cell. The interrogation cell is contained within the sample analysis and disposal subsystem 12 which preferably has a sealed surrounding protective enclosure 14. This subsystem 12 is sealed so that it is of the same pressure as duct 2. The exhaust gases from which the fly ash sample has been removed are then returned to the main duct 2 through duct 18 which in the form shown is downstream of duct 4.

It is preferred that the means for withdrawing fly ash containing exhaust gas from the main duct accomplishes withdrawal in such a manner that the sample will have a velocity and fly ash concentration generally equal to that of the main duct 2. Such systems are known to those skilled in the art.

The electronic processing system is shown within the dashed enclosure 26. The microwave subsystem 30 determines the carbon and fly ash weight of the fly ash samples introduced into the interrogation cell which is disposed within the sample analysis and disposal subsystem 12 with which it is in communication by electrical lead 32. The computer subsystem 36 is in communication with the sample analysis and disposal subsystem 14 by means of electrical lead 38. It is also in communication with the sample collection and handling subsystem 6 by means of electrical lead 40 and in communication with the microwave subsystem 30 by electrical lead 42. All of these connections are made through intermediate interface input/output subsystem 44 and electrical lead 48. The computer subsystem 36 is responsible for the integrated control of the other subsystems, as well as the calculation of the carbon content and the driving of the displays.

Figure 2:
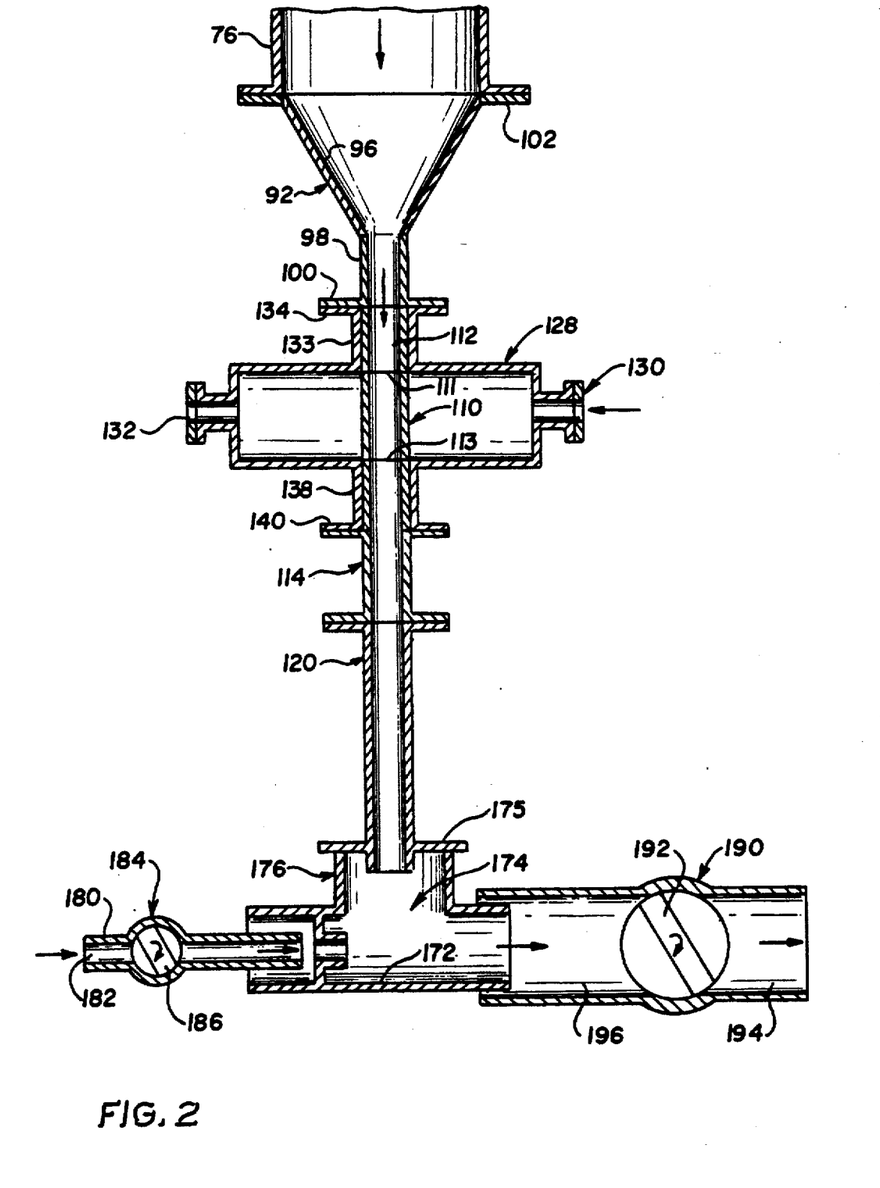
FIG. 2 is a partially schematic cross-sectional illustration showing an interrogation chamber of the present invention.

With reference to FIG. 2, a brief description of the system will be provided in order to enhance full comprehension of the system. The cycle of operation begins with the collection of a sample of fly ash in the delivery column 76 which is preferably the outlet portion of a cyclone separator. Delivery column 76 is in communication with and receives fly ash from the separator. Delivery column 76 is also in communication with underlying chamber 112 of the interrogation cell 110.

The fly ash collection system collection rate is determined by the concentration of fly ash in the duct F and the area of the sample probe. If it is desired to collect fly ash at an increased rate, the probe cross-section may be increased. For example, the system may be so configurated that the interrogation cell will receive 10 grams of fly ash and employ a three minute collection and interrogation time. If desired, increased speed could be employed to provide an update on carbon every minute.

Also shown within the dashed line enclosure 26 of FIG. 1 are the power supply subsystem 54 which is responsible for providing power at the correct voltage for use by the other subsystems. It also preferably contains means for establishing an uninterrupted power by means of power conditioner 60 of appropriate quality to the system in the event of AC voltage fluctuations or dropouts.

The power supply subsystem 54 preferably includes an uninterruptable AC power supply and several DC power supplies which provide power to the various system components. This serves to continue desired operation even during power fluctuations and sags and preserves time-average reading data on the total loss of power. It is preferred that the battery and the power supply be sized for about one-half hour of operation.

The enclosure environmental control system 58 controls the temperature of the electronics enclosure 26 and the purge air into the enclosure 26. The enclosure environmental control subsystem 58 may consist of an externally mounted air conditioner for temperature control combined with a fan and filter system to introduce clean purge air into enclosure 26. It is desired to maintain a temperature of generally about 80° F. to 90° F. within the enclosure 26 in order to reduce temperature-induced drift in the instruments and to enhance reliability.

The computer subsystem 36 through the input/output subsystem 44 is in communication with the meter assembly 62 through lead 64. The meter assembly 62 provides a visual indication of the carbon concentration, carbon flow rate and fly ash flow rate in order to permit the control room operator to employ this information in the operation of the boiler. The operator can select either instantaneous or average readings, as desired.

The sample collection and handling system 6 gathers the fly ash, preferably using an isokinetic probe inserted into the main flue gas duct 2. A suitable form of probe and sample collection system for the purpose is that disclosed in British patent 872,094. Although other systems may be employed for this purpose, a cyclone separator may be employed to separate the fly ash from the flue gas from duct 4 and return the flue gas to the duct through duct 18. It is preferred that the fly ash collect in the bottom of the separator and move it into the interrogation cell 110 under the influence of gravity. Suitable valves (not shown) well known to those skilled in the art may be employed to isolate the interrogation cell 110 from the negative pressure of the separator.

Referring once again to FIGS. 1 and 2, the fly ash removed from the gaseous stream in main duct 2 will drop under the influence of gravity into the delivery column 76 and be delivered by the entry column 92 to interrogation cell 110. The fly ash while in the interrogation cell 110 will be subjected to microwave radiation generated by microwave generator 130. Computer subsystem 36 also receives information regarding the amount of microwave energy presented to the sample, the amount of microwave energy passing through the fly ash sample and the amount of energy reflected from the sample. On the basis of this information, it computes the amount of microwave energy absorbed by the fly ash. This absorption amount which may be converted into the amount of carbon and the amount of fly ash.

This permits determination of both the amount of carbon in the fly ash and the percentage of carbon in the fly ash. The fly ash flow rate and carbon content are determined in the computer subsystem 36 and are fed through input/output subsystem 44 over lead 64 to meter assembly 62 which provides a visual readout for the benefit of an operator or may be stored and, if desired, may be employed to automatically adjust the boiler to produce less carbon.

Referring to FIG. 2 in greater detail there is shown the delivery column 76 from which fly ash will pass under the influence of gravity. The fly ash is received in column 92 which in the form shown has a downwardly tapered tubular upper portion 96, a generally cylindrical lower portion 98 and generally radially outwardly projecting annular flanges 100, 102. Microwave chokes 111, 113 are positioned respectively in the upper and lower ends of the portion of interrogation tube 110 within the fly ash sample being interrogated will be received. These chokes having an open mesh which will permit passage of fly ash particles of desired size therethrough. These chokes also resist undesired escape of microwaves from the effective interrogation volume which is the section of interrogation tube 110 between the chokes 111,113. The size of mesh opening in choke 113 will preferably be of the same size as those of choke 111. The openings, for example, may be on the order of about 1/8 to ¼ inch. The chokes 111, 113 are made of an electrically conductive material and are grounded to the microwave circuit.

The interrogation tube 110, which is preferably of rectangular cross-sectional shape, is composed of a material which permits the passage of microwaves therethrough, but not the passage of fly ash therethrough. Among the suitable materials for this purpose are glass, alumina, quartz, and materials available under the trade designations Teflon and Pyrex. Fly ash will descend preferably under the influence of gravity through the interior 112 of interrogation tube 110 into the effective interrogation volume defined by chokes 111, 113. This provides for a predetermined volume of fly ash to be tested.

Disposed in adjacent relationship with respect to interrogation tube 110 is an elongated waveguide 128 which has a longitudinal axis oriented generally perpendicularly with respect to the axis of the interrogation tube 110. The wave guide 128 may have a generally rectangular cross-sectional configuration. Microwave energy entering input 130 will pass through interrogation tube 110 and to the extent not absorbed by the fly ash disposed within the effective interrogation volume or reflected by the fly ash will be received at the output end 132. The waveguide 128, in the form shown, has an upwardly projecting tubular portion 133 which terminates in an annular flange 134 which is secured in intimate surface-to-surface contact with flange 100. Portion 133 is in surface-to-surface contact with the outer surface of interrogation tube 110. Similarly, downwardly projecting tubular portion 138 terminates in an annular flange 140 and is in surrounding surface-to-surface engagement with interrogation tube 110.

Eductor 174 which is hollow and defined by annular member 176 which is in intimate contact with annular flange 175 of tubular section 120 and the underlying annular portion 172.

During testing, the fly ash may be in the form of a column resting on element 172 of eductor and exiting up to choke 111 or may be supported on a closed valve (not shown) disposed within interrogation tube 110 underlying choke 113.

In order to withdraw the fly ash from the column 110 after interrogation has been accomplished, it is preferred to employ automated means. A source of pressurized air is in communication with tube 180 which defines passageway 182. When the eductor valve 184 is opened such that its passageway 186 is opened to and in communication with passageway 182, pressurized air enters the eductor and urges the fly ash in the direction indicated by the arrows. When the charge of fly ash disposed on element 172 of eductor 176 is to be discharged, the discharge valve 190 is also opened so that passageway 196 is opened with passageway 194 of discharge tube 196. Coordinated operation of the two valves 184, 190 will readily effect both opening and closing of the two valves in coordinated fashion.

The samples emerging from passageway 194 may be returned automatically to the main duct 2 employing the pressurized air and a partial vacuum on the downstream side created by the duct 2. If desired, further valving may be provided to facilitate withdrawal of a sample from the system for examination.

It will be appreciated that the movement of fly ash in a downwardly direction preferably under the influence of gravity will cause the fly ash sample to be exposed to microwave radiation. In a manner hereinbefore described and to be described in greater detail hereinafter, the amount of the power delivered (PF) to the fly ash which is absorbed by the fly ash is determined by measuring the amount of microwave radiation reflected off (PR) of the fly ash and passing through the fly ash (PT). The amount of microwave energy absorbed permits a determination of the amount of carbon in the fly ash, the amount of fly ash, and the carbon concentration.

The microwave is preferably at a frequency of about 2,450 MHz. This may be supplied by the microwave generator by any conventional means.

In operation of the system as shown in FIG. 2, fly ash is continually fed to interrogation chamber 110 at the rate it is collected by the sample collection and handling system. The computer subsystem 36 continuously monitors the microwave power reflected and the microwave power transmitted. When fly ash in interrogation cell 110 reaches the bottom of waveguide 128, i.e., the level of choke 113, the computer subsystem 36 picks up a change in the j reflected power and power transmitted and records a start time. The reflected power and transmitted power continues to vary until the level of the fly ash in interrogation cell 110 reaches the top of waveguide 128, i.e., the level of choke 111. At that time computer subsystem 36 records a stop time and records the reflected power and transmitted power. These final readings may be employed to calculate the carbon 1 weight, carbon concentration and fly ash glass weight. The elapsed time between the start time and stop time may be employed to calculate sample system (collection rate). As the sample collection rate is proportional to the flow rate in duct F, a duct flow rate for carbon and fly ash may be calculated by the computer subsystem 36. The computer subsystem then initiates a purge cycle to remove the fly ash sample from interrogation cell 110.

Assuming for purposes of example, as is generally the case that the fly ash has two primary components, i.e., fly ash glass and carbon that respond to microwave these components, will each reflect and absorb microwave power. For such a sample, the power transmitted (PT) may be determined in accordance with Equation 1.

$$PT = (FAGwt \times a1) + (Cwt \times b1) + K1 \qquad \text{Equation 1}$$

The power reflected may be determined by Equation 2.

$$PR = (FAGwt \times a2) + (Cwt \times b2) + K2 \qquad \text{Equation 2}$$

Wherein:
PT = Power Transmitted Through the Sample
PR = Power Reflected By the Sample
FAGwt = Fly Ash Glass Weight
Cwt = Carbon Weight
a1, a2, b1 and b2 = Absorbability Coefficients
K1 and K2 = Interrogation Chamber and Equipment Losses Tests were performed on samples having different carbon contents to determine values for these coefficients and constants. These tests produced the following values:

$a1 = 0.027 \qquad b2 = 0.159$
$a2 = 0.012 \qquad k1 = 0.277$
$b1 = 0.047 \qquad k2 = 0.444$ By solving Equations 1 and 2, the values of FAGwt and Cwt for a particular PF level and interrogation chamber geometry may be determined.

Carbon concentration may be determined by Equation 3.

$$\text{Carbon Concentration (\%)} = Cwt / Cwt\& FAGwt \qquad \text{Equation 3}$$

The duct carbon flow rate may be calculated by Equations 4 through 6.

$$\text{Duct Carbon Rate} = CCD \times vD \times AD \qquad \text{Equation 4}$$

$$\text{Sampler Carbon Rate} = CCS \times vS \times AS \qquad \text{Equation 5}$$

Wherein
CCD = Carbon Concentration in Duct
VD = Duct Velocity F
AD = Duct Area
CCS = Carbon Concentration in Samples Probe
VS = Sampler Probe Velocity
AS = Sampler Probe Area As CCD equals CCS and vD equals vS, then $$\text{Duct Carbon Rate} = (\text{Sample Carbon Rate} \times AD)/AS \qquad \text{Equation 6}$$

In a similar manner, the system of the present invention may be employed to calculate the duct fly ash flow rate.

Figure 3:
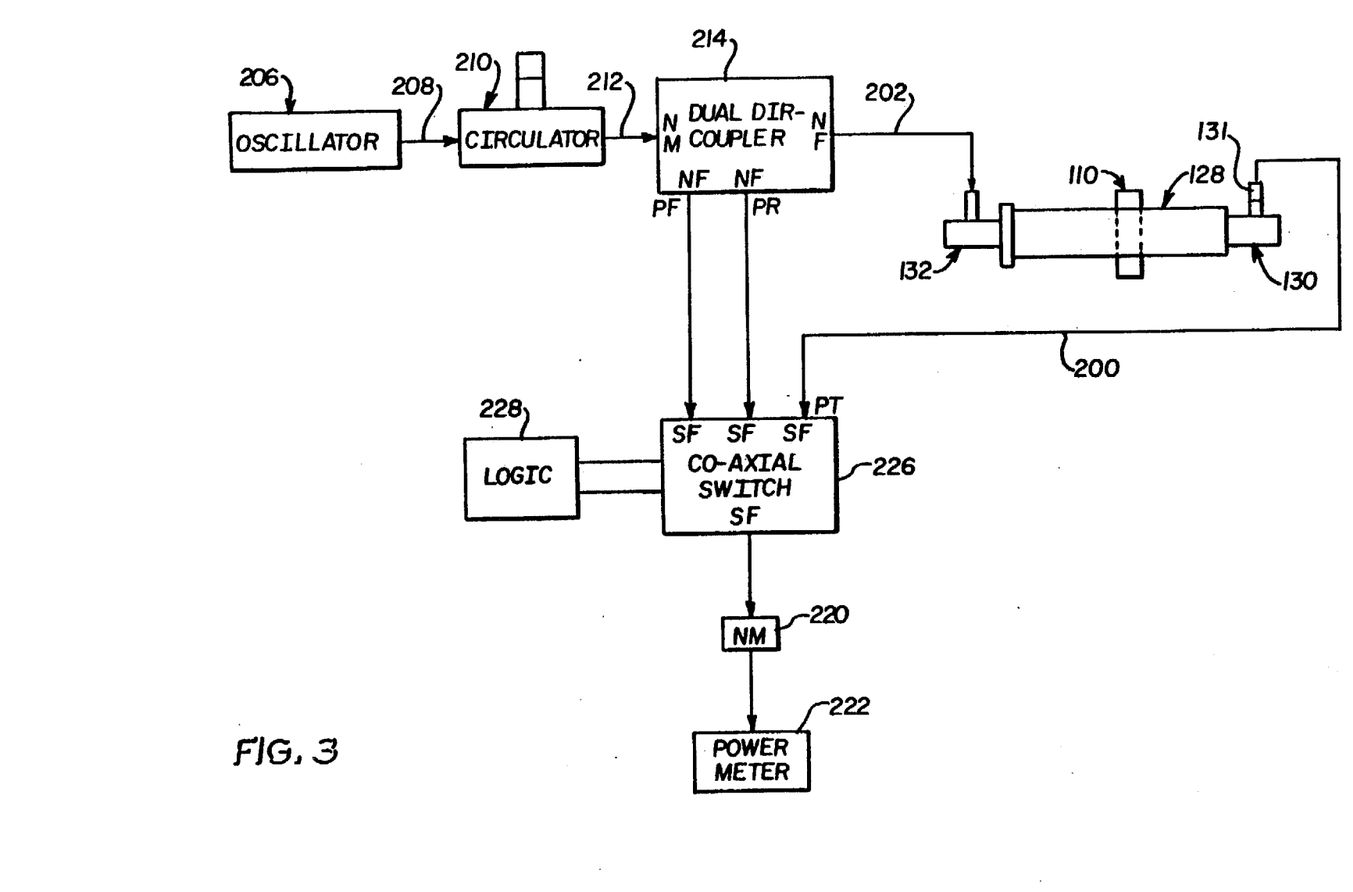
FIG. 3 is a block diagram of the microwave subsystem.

Referring in greater detail to FIG. 3, the microwave subsystem 30 will be described. As is shown in the upper right-hand portion of FIG. 3, the waveguide 128 has a first electrical lead 200 secured to the input 130 through attenuator 131 and a second electrical lead 202 secured to the output 132.

In the operation of this subsystem, the oscillator 206 generates microwave energy preferably at about 2,450 MHz frequency which is conducted by lead 208 to circulator 210 which allows the forward power to pass toward the waveguide 128 and by lead 212 to dual directional coupler 214 which is connected with waveguide outlet 132 by cable 202. The dual directional coupler 214 distinguishes between forward power and reflected power. The input sensor 220 of the power meter 222 is connected by coaxial switch assembly 226 to the transmitted power pickoff PT, the reflected power pickoff PR, and the forward power pickoff PF. Logic unit 228 which is part of computer subsystem 36 (FIG. 1) serves to control operation of the switch 226 to provide the desired mode. The computer subsystem 36 operates coaxial switch 226 to determine microwave power forward, reflected power, and power transmitted through the sample.

The carbon of the sample is equal to the carbon weight divided by the sample weight. The sample weight in turn is equal to the carbon weight plus the fly ash weight.

The sample analyzer and disposal subsystem 12 contains the interrogation cell 110.

The input/output subsystem 44 and the computer subsystem 36 preferably contain a microprocessor which may be programmed in any language in a manner well known to those skilled in the art. It will preferably be retained in EPROM or battery-packed RAM. The input/output subsystem 44 serves to provide interfaces with the computer subsystem 36 and the other various subsystems. A brief description of the system will be provided in order to enhance full comprehension of the system. The cycle of operation begins with the collection of a sample of fly ash in the holdup column 76 which is in communication with and receives fly ash from the separator and the chamber 112, 116 of the interrogation cell 110.

The quantity of sample introduced into the holdup column 76 is continuously fed from holdup column 76. The air control valve for the sample metering valves is preferably a 24 VDC solenoid operated valve.

Figure 4:
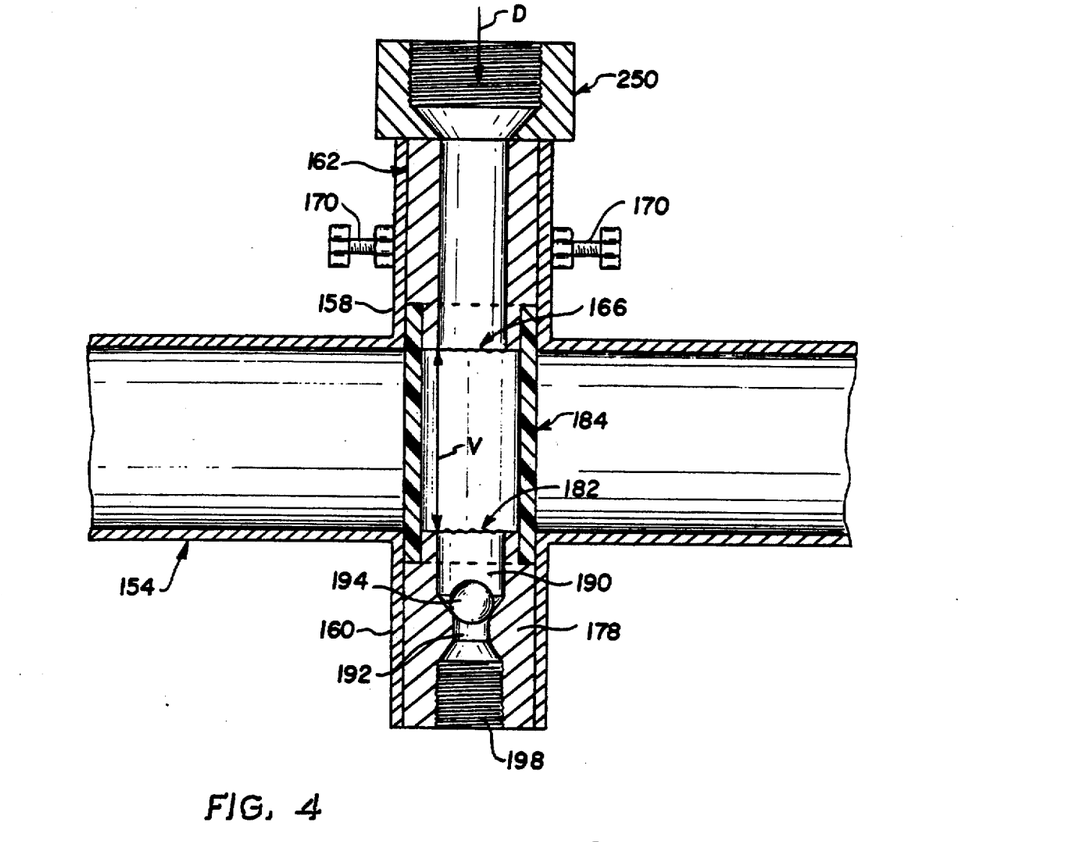
FIG. 4 is a schematic cross-sectional illustration of a modified system of the present invention.

Referring to FIG. 4, there is shown a modified system for removing fly ash from the interrogation chamber after it has been tested. Fly ash enters the system through delivery tube 250 in the direction indicated by arrow D. Microwave guide 154 has upwardly and downwardly directed extensions 158, 160. A tubular insert 162 is disposed within extension 162 and is in intimate contact therewith. Insert 162 is preferably composed of brass or another electrically conductive material. At the lower extremity of insert 162 is choke 166. Electrical contacts 170, 172 are respectively secured to the insert 162 and upper extension 158. Similarly, insert 178 is disposed interiorly of lower extension 160 and supports choke 182. Interrogation tube 184 has its ends received within recesses of inserts 158, 160. The effective interrogation volume V is the distance between opposed interior walls of waveguide 154 which is generally equal to the distance between the chokes 166, 182.

Insert 178 also serves as a valve. An upwardly open recess 190 is in communication with a lower passageway 192. A ball valve element 194 is normally seated in recess 190 by gravity to close passageway 192 and block communication with recess 190. When ball element 194 is in the seated position as shown in FIG. 4, the fly ash will have its column supported on the valve. When the test has been completed, in this embodiment, the fly ash is withdrawn by introducing compressed air through opening 198 to unseat valve element 194 and blowing the fly ash out through delivery tube 250 The next cycle of testing may then be initiated. This embodiment eliminates the need for eductor 174 of the other embodiment.

If desired, a vibrator may be employed to consolidate the fly ash sample within the effective interrogation volume.

It will be appreciated therefore that the apparatus and method of the present invention provide an efficient means for measuring the carbon content of a batch of fly ash in a rapid automated manner.

Whereas particular embodiments of the invention have been described above for purposes of illustration, it will be evident to those skilled in the art that numerous variations of the details may be made without departing from the invention as defined in the appended claims.

We claim:

1. A method for determining carbon content in fly ash comprising,
providing a source of fly ash,
providing a microwave interrogation chamber and a source of microwave power in communication therewith,
introducing a quantity of said fly ash into said interrogation chamber,
exposing said fly ash to microwave power for interrogation of said fly ash for a predetermined period of time while resisting undesired discharge of said microwave power, and
determining the amount of carbon in said fly ash by determining the amount of said microwave power absorbed by said fly ash through measurement of the amount of said microwave power transmitted through said fly ash and measurement of the amount of said microwave power reflected by said fly ash, whereby the amount of carbon in said fly ash may be determined without regard to any other properties of said fly ash.

2. The method of claim 1 including,
determining the carbon concentration of said fly ash by determining the weight of said fly ash and determining the amount of said carbon content as related to said weight.

3. The method of claim 2 including,
employing boiler exhaust gases as a source of said fly ash, and
separating said fly ash from said exhaust gas.

4. The method of claim 1 including,
introducing predetermined quantities of fly ash into said microwave interrogation chamber, and
withdrawing said fly ash from said chamber after said microwave power exposure and before introducing the next charge of fly ash into said microwave interrogation chamber.

5. The method of claim 4 including,
providing at least one sample obtaining means for withdrawing fly ash containing exhaust gas from a main duct in such manner as to have a sample with a velocity and fly ash concentration generally equal to that of the main duct.

6. The method of claim 5 including,
providing a generally vertically oriented fly ash delivery conduit which is oriented generally perpendicular to the path of microwave power, and
delivering said fly ash to said microwave interrogation chamber under the influence of gravity.

7. The method of claim 6 including,
maintaining said fly ash in a stationary position during interrogation by said microwave power.

8. The method of claim 7 including,
after determining the weight of the carbon in said interrogated fly ash removing said fly ash from the analysis area by pneumatic means.

9. The method of claim 4 including,
providing computer means for determining the carbon concentration of said fly ash, and
delivering to said computer means information regarding the amount of microwave power passing through said fly ash and the amount of said microwave power reflected by said fly ash.

10. The method of claim 9 including,
employing said computer means to determine the amount of said microwave power absorbed by said fly ash.

11. The method of claim 10 including,
employing said computer means to determine the concentration of said carbon in said fly ash on a percentage weight basis.

12. The method of claim 4 including,
providing a boiler exhaust duct as said fly ash source, and
determining the fly ash flow rate within said duct.

13. The method of claim 4 including,
providing said fly ash with fly ash glass and carbon content, and
determining the amount of said fly ash glass and carbon in said fly ash.

14. The method of claim 12 including,
said predetermined period of time being the period during which the amount of said fly ash exposed to said microwave power increases to a maximum.

15. The method of claim 4 including,
testing a predetermined volume of said fly ash within said interrogation chamber.

16. The method of claim 15 including,
employing a microwave waveguide having a longitudinal axis oriented generally perpendicular with respect to said microwave interrogation chamber as the source of said microwave power, and
establishing said predetermined volume of a height generally equal to the height of the interior opening of said microwave waveguide.

17. The method of claim 15 including,
said process being a batch process.

18. The method of claim 1, including
providing choke means for resisting undesired discharge of said microwave power at or adjacent the ends of the portion of said interrogation chamber means within which said quantity of fly ash being exposed to said microwave power is interrogated.

19. Apparatus for measuring the carbon content in fly ash comprising,
fly ash supply means for supplying said fly ash,
interrogation chamber means for receiving said fly ash,
microwave generating means for exposing said fly ash to interrogation by microwave power,
microwave guide means operatively associated with said microwave generating means for resisting undesired discharge of said microwave power, and
computer means for determining the carbon content of said fly ash and the weight of said fly ash from the amount of said microwave power transmitted through said fly ash and the amount of said microwave power reflected by said fly ash, whereby the amount of carbon in said fly ash may be determined without regard to any other properties of said fly ash.

20. The apparatus of claim 19 including,
said computer means having means for employing said microwave reflected and transmitted through information to determine the amount of microwave power absorbed by said fly ash.

21. The apparatus of claim 20 including,
means for determining the level of fly ash within said interrogation means.

22. The apparatus of claim 21 including,
pneumatic means for removing said interrogated fly ash from said apparatus.

23. The apparatus of claim 22 including,
said means for fly ash removal including pneumatic means and discharge valve means.

24. The apparatus of claim 22, including
said interrogation chamber means including an interrogation tube for receiving said fly ash, and
said microwave guide means having a microwave waveguide oriented generally perpendicular with respect to said interrogation tube.

25. The apparatus of claim 23 including,
said microwave guide having an input end and an output end.

26. The apparatus of claim 24 including,
said interrogation means having a choke means for resisting undesired discharge of microwave radiation therethrough.

27. The apparatus of claim 26 including.
said means for determining the amount of microwave power being reflected by said fly ash including dual coupler means.

28. The apparatus of claim 26 including,
said interrogation tube being composed of a material which permits passage of microwave power therethrough.

29. The apparatus of claim 26 including,
said computer means having means for monitoring the time interval as said interrogation means fills with said fly ash between when said fly ash has minimum exposure until it has maximum exposure to said microwave radiation.

30. The apparatus of claim 26 including,
said choke means have two chokes disposed in relative spaced relationship within said chamber means.

31. The apparatus of claim 30 including,
said microwave guide having an interior opening of a height generally equal to the spacing between said chokes, whereby said chokes will define an effective interrogation volume.

32. The apparatus of claim 30, wherein
said choke means disposed at or adjacent the ends of the portion of said interrogation chamber means within which said fly ash which is being exposed to said microwave power is interrogated.

* * * * *

UNITED STATES PATENT AND TRADEMARK OFFICE
CERTIFICATE OF CORRECTION

PATENT NO. : 5,109,201
DATED : April 28, 1992
INVENTOR(S) : DOUGLAS N. TRERICE AND CHARLES R. BUFFLER It is certified that error appears in the above-identified patent and that said Letters Patent is hereby corrected as shown below:

Column 2, line 50, "i" should be deleted.

Column 5, line 28, "1/8 to 1/8 inch" should be -- 1/8 to 3/16 inch --.

Column 6, line 48, "j" should be deleted.

Claim 21, column 11, line 10, -- chamber -- should be inserted after "interrogation".

Claim 26, column 11, line 27, -- chamber -- should be inserted after "interrogation".

Claim 29, column 12, line 11, -- chamber -- should be inserted after "interrogation".

Claim 30, column 12, line 17, -- interrogation -- should be inserted after "said".

Signed and Sealed this

Fourteenth Day of March, 1995

Attest:

BRUCE LEHMAN

*Attesting Officer*  *Commissioner of Patents and Trademarks*